(12) United States Patent
Dandekar et al.

(10) Patent No.: US 6,888,037 B2
(45) Date of Patent: May 3, 2005

(54) PROCESS FOR PRODUCING CUMENE

(75) Inventors: Ajit B. Dandekar, South Plainfield, NJ (US); Michael Hryniszak, Bordentown, NJ (US); David Lawrence Stern, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/319,161

(22) Filed: Dec. 13, 2002

(65) Prior Publication Data

US 2003/0092949 A1 May 15, 2003

Related U.S. Application Data

(62) Division of application No. 09/902,957, filed on Jul. 11, 2001, now abandoned.

(51) Int. Cl.$^7$ ................................................. C07C 2/66
(52) U.S. Cl. ........................ 585/467; 585/475; 585/323
(58) Field of Search ................................ 585/467, 475, 585/323

(56) References Cited

U.S. PATENT DOCUMENTS

| | | | |
|---|---|---|---|
| 3,308,069 A | 3/1967 | Wadlinger et al. | 252/455 |
| 3,966,644 A | 6/1976 | Gustafson | 252/455 R |
| 4,185,040 A | 1/1980 | Ward et al. | 585/467 |
| 4,328,130 A | 5/1982 | Kyan | 252/477 R |
| 4,439,409 A | 3/1984 | Puppe et al. | 423/328 |
| 4,441,990 A | 4/1984 | Huang | 208/111 |
| 4,798,816 A | 1/1989 | Ratcliffe et al. | 502/62 |
| 4,826,667 A | 5/1989 | Zones et al. | 423/277 |
| 4,954,325 A | 9/1990 | Rubin et al. | 423/328 |
| 4,992,606 A | 2/1991 | Kushnerick et al. | 585/467 |
| 5,236,575 A | 8/1993 | Bennett et al. | 208/46 |
| 5,250,277 A | 10/1993 | Kresge et al. | 423/329.1 |
| 5,258,565 A * | 11/1993 | Kresge et al. | 585/467 |
| 5,362,687 A | 11/1994 | Tokunaga | 501/21 |
| 5,723,710 A | 3/1998 | Gajda et al. | 585/467 |
| 2002/0038067 A1 | 3/2002 | Dandekar et al. | 585/467 |
| 2002/0042548 A1 | 4/2002 | Dandekar et al. | 585/446 |

FOREIGN PATENT DOCUMENTS

WO   WO/0719750   7/1996

\* cited by examiner

*Primary Examiner*—Thuan D Dang
(74) *Attorney, Agent, or Firm*—Darryl M. Tyus; Linda A. Kubena

(57) ABSTRACT

A process for producing cumene is provided which comprises the step of contacting benzene and propylene under at least partial liquid phase alkylating conditions with a particulate molecular sieve alkylation catalyst, wherein the particles of said alkylation catalyst have a surface to volume ratio of about 80 to less than 200 inch$^{-1}$.

6 Claims, No Drawings

PROCESS FOR PRODUCING CUMENE

This application is a divisional of U.S. application Ser. No. 09/902,957, filed Jul. 11, 2001, now abandoned.

FIELD OF THE INVENTION

The present invention relates to a process for producing cumene.

BACKGROUND OF THE INVENTION

Cumene is a valuable commodity chemical which is used industrially for the production of phenol and acetone. Cumene has for many years been produced commercially by the alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 describes the use of MCM-22 in the alkylation of benzene with propylene.

Typically, the zeolite catalysts employed in hydrocarbon conversion processes, such as aromatics alkylation, are in the form of cylindrical extrudates. However, it is known from, for example, U.S. Pat. No. 3,966,644 that shaped catalyst particles having a high surface to volume ratio, such as those having a polylobal cross-section, can produce improved results in processes which are diffusion limited, such as the hydrogenation of resid.

Moreover, it is known from U.S. Pat. No. 4,441,990 that a polylobal catalyst particle having a non-cylindrical centrally located aperture can reduce the diffusion path for reagents and the pressure drop across packed catalyst beds while minimizing catalyst loss due to breakage, abrasion and crushing. In particular, Example 8 of the '990 patent discloses that hollow trilobal and quadrilobal ZSM-5 catalysts are more active and selective for the ethylation of benzene at 770° F. and 300 psig pressure than solid cylindrical catalysts of the same length. Under these conditions, the reagents are necessarily in the vapor phase.

Recently, attention has focused on liquid phase alkylation processes for producing alkylaromatic compounds, since liquid phase processes operate at a lower temperature than their vapor phase counterparts and hence tend to result in lower yields of by-products. Work by the present inventors has shown that shaped catalyst particles, such as those disclosed in U.S. Pat. Nos. 3,966,644 and 4,441,990 show little or no advantage when used in the liquid phase ethylation of benzene. Surprisingly, however, it has now been found that shaped catalyst particles can yield improved results in the liquid phase propylation of benzene to produce cumene.

SUMMARY OF THE INVENTION

In one aspect, the present invention resides in a process for producing cumene which comprises the step of contacting benzene and propylene under at least partial liquid phase alkylating conditions with a particulate molecular sieve alkylation catalyst, wherein the particles of said alkylation catalyst have a surface to volume ratio of about 80 to less than 200 inch$^{-1}$.

Preferably, the particles of said alkylation catalyst have a surface to volume ratio about 100 to about 150 inch$^{-1}$.

Preferably, the molecular sieve of the alkylation catalyst is selected from MCM-22, PSH-3, SSZ-25, MCM-36, MCM-49, MCM-56, faujasite, mordenite and zeolite beta.

Preferably, said alkylating conditions include a temperature of about 10° C. to about 125° C., a pressure of about 1 to about 30 atmospheres, and a benzene weight hourly space velocity (WHSV) of about 5 hr$^{-1}$ to about 50 hr$^{-1}$.

In a further aspect, the present invention relates to a process for producing cumene which comprises the steps of:

i) contacting benzene and propylene with a particulate molecular sieve alkylation catalyst under at least partial liquid phase alkylating conditions to provide a product containing cumene and a polyisopropylbenzene fraction;

ii) separating the polyisopropylbenzene fraction from the product; and iii) contacting the polyisopropylbenzene fraction and benzene with a particulate molecular sieve transalkylation catalyst under at least partial liquid phase transalkylating conditions, wherein the particles of at least said alkylation catalyst have a surface to volume ratio of about 80 to less than 200 inch$^{-1}$.

Preferably, the molecular sieve of the transalkylation catalyst is selected from MCM-22, PSH-3, SSZ-25, MCM-36, MCM-49, MCM-56, ZSM-5, faujasite, mordenite and zeolite beta.

Preferably, said transalkylating conditions include a temperature of about 100° C. to about 200° C.; a pressure of 20 to 30 barg, a weight hourly space velocity of 1 to 10 on total feed and benzene/polyisopropylbenzene weight ratio 1:1 to 6:1.

DETAILED DESCRIPTION OF THE INVENTION

The present invention is directed to a process for producing cumene by reacting benzene with propylene under at least partial liquid phase conditions in the presence of a particulate molecular sieve alkylation catalyst, wherein the particles of the alkylation catalyst have a surface to volume ratio of about 80 to less than 200 inch$^{-1}$, preferably, about 100 to about 150 inch$^{-1}$.

According to the invention, it has now been found that the liquid phase propylation of benzene, unlike the liquid phase ethylation of benzene, is sensitive to intraparticle (macroporous) diffusion limitations. In particular, by selecting the shape and size of the particles of the alkylation catalyst such that the surface to volume ratio is within the specified range, it is found that the intraparticle diffusion distance can be decreased without excessively increasing the pressure drop across the first catalyst bed. As a result, the activity of the catalyst for the propylation of benzene can be increased, while at the same time the selectivity of the catalyst towards undesirable polyalkylated species, such as diisopropylbenzene (DIPB) can be reduced.

Producing the alkylation catalyst with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. For example, a cylindrical catalyst particle having a diameter of 1/32 inch and a length of 3/32 inch has a surface to volume ratio of 141, whereas a quadralobal solid extrudate having the external shape disclosed in FIG. 4 of U.S. Pat. No. 4,441,990 and having a maximum cross-sectional dimension of 1/16 inch and a length of 3/16 inch has a surface to volume ratio of 128. A hollow tubular extrudate having an external diameter of ¹⁄₁₀ inch, an internal diameter of ¹⁄₃₀ inch and a length of ³⁄₁₀ inch has a surface to volume ratio of 136.

The alkylation catalyst used in the process of the invention comprises a crystalline molecular sieve selected from MCM-22 (described in detail in U.S. Pat. No. 4,954,325), PSH-3 (described in detail in U.S. Pat. No. 4,439,409), SSZ-25 (described in detail in U.S. Pat. No. 4,826,667), MCM-36 (described in detail in U.S. Pat. No. 5,250,277), MCM-49 (described in detail in U.S. Pat. No. 5,236,575), MCM-56 (described in detail in U.S. Pat. No. 5,362,697), faujasite, mordenite, and zeolite beta (described in detail in U.S. Pat. No. 3,308,069). The molecular sieve can be combined in conventional manner with an oxide binder, such as alumina, such that the final alkylation catalyst contains between 2 and 80 wt % sieve.

The alkylation process of the invention is conducted under conditions such that both the benzene and propylene are under at least partial liquid phase conditions. Suitable conditions include a temperature of up to about 250° C., e.g., up to about 150° C., e.g., from about 10° C. to about 125° C.; a pressure of about 250 atmospheres or less, e.g., from about 1 to about 30 atmospheres; a benzene to propylene ratio of about 1 to about 10 and a benzene weight hourly space velocity (WHSV) of from about 5 $hr^{-1}$ to about 250 $hr^{-1}$, preferably from 5 $hr^{-1}$ to 50 $hr^{-1}$.

Although the alkylation process of the invention is particularly selective towards the production of the desired monoalkylated species, cumene, the alkylation step will normally produce some polyalkylated species. Thus the process preferably includes the further steps of separating the polyalkylated species from the alkylation effluent and reacting them with additional benzene in a transalkylation reactor over a suitable transalkylation catalyst. Preferably, the transalkylation reaction is conducted in a separate reactor from the alkylation reaction.

The transalkylation catalyst is preferably a molecular sieve which is selective to the production of the desired monoalkylated species and can, for example employ the same molecular sieve as the alkylation catalyst, such as MCM-22, PSH-3, SSZ-25, MCM-36, MCM-49, MCM-56 and zeolite beta. In addition, the transalkylation catalyst may be ZSM-5, zeolite X, zeolite Y, and mordenite, such as TEA-mordenite. Preferably, the transalkylation catalyst is also arranged to have a surface to volume ratio of about 80 to less than 200 $inch^{-1}$, and more preferably about 100 to about 150 $inch^{-1}$.

The transalkylation reaction of the invention is conducted in the liquid phase under suitable conditions such that the polyalkylated aromatics react with the additional benzene to produce additional cumene. Suitable transalkylation conditions include a temperature of 100 to 200° C., a pressure of 20 to 30 barg, a weight hourly space velocity of 1 to 10 on total feed and benzene/PIPB weight ratio 1:1 to 6:1.

The alkylation and transalkylation steps of the process of the invention can be conducted in an suitable reactor, such as a fixed or moving bed or a catalytic distillation unit.

The following Examples will serve to further illustrate the process and some advantages of the present invention. In the Examples, catalyst performance is defined by reference to the kinetic rate constant which is determined by assuming second order reaction kinetics. For a discussion of the determination of the kinetic rate constant, reference is directed to "Heterogeneous Reactions: Analysis, Examples, and Reactor Design, Vol. 2: Fluid-Fluid-Solid Reactions" by L. K. Doraiswamy and M. M. Sharma, John Wiley & Sons, New York (1994) and to "Chemical Reaction Engineering" by O. Levenspiel, Wiley Eastern Limited, New Delhi (1972).

EXAMPLE 1

Benzene alkylation with propylene was conducted using a conventionally prepared MCM-49 catalyst. The catalyst was prepared by extruding a mixture of 80 wt % MCM-49 crystal and 20 wt % alumina into solid cylindrical extrudates having a diameter of ¹⁄₁₆ inch and a length of ¼ inch. The resultant catalyst particles had a surface to volume ratio of 72.

One gram of the catalyst was charged to an isothermal well-mixed Parr autoclave reactor along with a mixture comprising of benzene (156 g) and propylene (28 g). The reaction was carried out at 266° F. (130° C.) and 300 psig for 4 hours. A small sample of the product was withdrawn at regular intervals and analyzed by gas chromatography. The catalyst performance was assessed by a kinetic activity rate constant based on propylene conversion and cumene selectivity at 100% propylene conversion. The results are described in Table 1.

EXAMPLE 2

The process of Example 1 was repeated with the catalyst being produced by extruding the mixture of 80 wt % MCM-49 crystal and 20 wt % alumina into solid quadralobal extrudates having a maximum cross-sectional dimension of ¹⁄₂₀ inch and a length of ¼ inch. The resultant catalyst particles had a surface to volume ratio of 120.

When tested for the propylation of benzene under the conditions used in Example 1, the catalyst of Example 2 gave the results shown in Table 1.

TABLE 1

| Catalyst | Kinetic Rate Constant | DIPB/Cumene (wt %) |
|---|---|---|
| Example 1 | 185 | 14.6 |
| Example 2 | 240 | 12.8 |

It will be seen from Table 1 that the shaped catalyst of Example 2 exhibits higher activity and lower selectivity to undesirable DIPB than the cylindrical catalyst of Example 1.

What we claim is:

1. A process for producing cumene which comprises the step of contacting benzene and propylene with a particulate molecular sieve alkylation catalyst having a catalytic activity under at least partial liquid phase alkylating conditions to provide a product comprising cumene and a polyisopropylbenzene fraction, said particulate molecular sieve alkylation catalyst comprising MCM-49 having a surface to volume ratio of about 120 $inch^{-1}$; and wherein said catalytic activity of said particulate molecular sieve alkylation catalyst is greater than that of a molecular sieve alkylation catalyst having a surface to volume ratio of less than about 80 $inch^{-1}$.

2. A process for producing cumene which comprises the steps of:
   i) contacting benzene and propylene with a particulate molecular sieve alkylation catalyst under at least partial liquid phase alkylating conditions to provide a product containing cumene and a polyisopropylbenzene fraction, wherein the molecular sieve of the alkylation catalyst is MCM-49
   ii) separating the polyisopropylbenzene fraction from the product; and
   iii) contacting the polyisopropylbenzene fraction and benzene with a transalkylation catalyst under at least partial liquid phase transalkylating conditions,
wherein the particles of at least said alkylation catalyst have a surface to volume ratio of about 120 $inch^{-1}$.

3. The process of claim 2 wherein said alkylating conditions include a temperature of about 10° C. to about 125° C., a pressure of about 1 to about 30 atmospheres, and a benzene weight hourly space velocity (WHSV) of about 5 $hr^{-1}$ to about 50 $hr^{-1}$.

4. The process of claim 2 wherein the particles of said transalkylation catalyst have a surface to volume ratio of about 80 to less than 200 $inch^{-1}$.

5. The process of claim 2 wherein the transalkylation catalyst comprises a molecular sieve selected from the group consisting of MCM-22, PSH-3, SSZ-25, MCM-36, MCM-49, MCM-56, ZSM-5, faujasite, mordenite and zeolite beta.

6. The process of claim 2 wherein said transalkylating conditions include a temperature of about 100° C. to about 200° C.; a pressure of 20 to 30 barg, a weight hourly space velocity of 1 to 10 $hr^{-1}$ on total feed and benzene/polyisopropylbenzene weight ratio 1:1 to 6:1.

* * * * *